(12) United States Patent
Childers, II et al.

(10) Patent No.: US 8,147,673 B2
(45) Date of Patent: Apr. 3, 2012

(54) SYSTEM AND PROCESS FOR TREATMENT AND DE-HALOGENATION OF BALLAST WATER

(75) Inventors: Harold E. Childers, II, Houston, TX (US); Randolto Fernandez, Houston, TX (US); Rudolf C. Matousek, Richmond, TX (US); James B. Moore, Katy, TX (US); David W. Hill, Sugar Land, TX (US)

(73) Assignee: Severn Trent De Nora, LLC, Sugar Land, TX (US)

( * ) Notice: Subject to any disclaimer, the term of this patent is extended or adjusted under 35 U.S.C. 154(b) by 1325 days.

(21) Appl. No.: 11/757,315

(22) Filed: Jun. 1, 2007

(65) Prior Publication Data

US 2008/0149485 A1 Jun. 26, 2008

Related U.S. Application Data

(63) Continuation-in-part of application No. 11/037,642, filed on Jan. 18, 2005.

(51) Int. Cl.
*C02F 1/461* (2006.01)
*C25B 1/26* (2006.01)
*C25B 1/24* (2006.01)

(52) U.S. Cl. ......... 205/743; 205/500; 205/501; 205/556

(58) Field of Classification Search ................. 205/701, 205/687, 743, 500, 501, 556; 210/756, 757; 204/228.6
See application file for complete search history.

(56) References Cited

U.S. PATENT DOCUMENTS

| | | |
|---|---|---|
| 1,944,803 A | 1/1934 | Ornstein |
| 4,009,104 A | 2/1977 | Behrendt et al. |
| 4,097,358 A | 6/1978 | Wiseman |

(Continued)

FOREIGN PATENT DOCUMENTS

CN  1064253 A  9/1992

(Continued)

OTHER PUBLICATIONS

Kim et al, "Effective control of chlorination and dechlorination at wastewater treatment plants using redox potential," Water Environment Research, vol. 69, No. 5, Jul./Aug. 1997, pp. 1008-1014.*

(Continued)

*Primary Examiner* — Keith Hendricks
*Assistant Examiner* — Colleen M Raphael
(74) *Attorney, Agent, or Firm* — D'Ambrosio & Menon, PLLC

(57) ABSTRACT

A system and process for de-halogenating ballast water before releasing the ballast water from the vessel. In one embodiment, the system comprises a means for measuring the halogen content of the ballast water, a reducing agent source in fluid communication with the ballast water, and a means for controlling the amount of reducing agent supplied to the ballast water. In one aspect, the means for measuring the halogen content comprises one or more oxidation/reduction potential analyzers. In another embodiment, the system comprises one or more hypochlorite electrolytic cells for generating hypochlorite to treat the ballast water.

One embodiment of the process for de-halogenating ballast water comprises measuring the oxidation/reduction potential of the ballast water and adding one or more reducing agents to the ballast water to de-halogenate the ballast water in response to the measured oxidation/reduction potential. In one aspect, the oxidation/reduction potential is modulated so that excess reducing agent is present in the ballast water.

17 Claims, 6 Drawing Sheets

U.S. PATENT DOCUMENTS

| | | | |
|---|---|---|---|
| 4,118,307 A | 10/1978 | LaBarre | |
| 4,179,347 A | 12/1979 | Krause et al. | |
| 4,248,690 A | 2/1981 | Conkling | |
| 4,260,463 A | 4/1981 | Rideout | |
| 4,767,511 A | 8/1988 | Aragon | |
| 4,952,298 A | 8/1990 | Bouche-Pillon et al. | |
| 5,000,006 A | 3/1991 | Itoh et al. | |
| 5,045,214 A | 9/1991 | Walker | |
| 5,082,573 A | 1/1992 | Goldstein et al. | |
| 5,348,664 A | 9/1994 | Kim et al. | |
| 5,443,991 A | 8/1995 | Godec et al. | |
| 5,816,181 A | 10/1998 | Sherman, Jr. | |
| 5,985,155 A | 11/1999 | Maitland | |
| 5,993,669 A * | 11/1999 | Fulmer | 205/501 |
| 6,125,778 A | 10/2000 | Rodden | |
| 6,221,262 B1 * | 4/2001 | MacDonald et al. | 210/757 |
| 6,315,886 B1 * | 11/2001 | Zappi et al. | 204/228.6 |
| 6,328,875 B1 * | 12/2001 | Zappi et al. | 205/500 |
| 6,402,932 B1 | 6/2002 | Bremer et al. | |
| 6,423,234 B1 | 7/2002 | Martin | |
| 6,488,835 B1 * | 12/2002 | Powell | 205/757 |
| 6,516,738 B2 | 2/2003 | Cannon | |
| 6,632,347 B1 | 10/2003 | Buckley et al. | |
| 6,761,815 B2 | 7/2004 | Nakajima et al. | |
| 6,773,607 B2 | 8/2004 | Russell | |
| 6,773,611 B2 | 8/2004 | Perlich et al. | |
| 6,923,901 B2 | 8/2005 | Leffler et al. | |
| 7,025,889 B2 | 4/2006 | Brodie | |
| 2002/0170816 A1 | 11/2002 | Leffler et al. | |
| 2003/0015481 A1 | 1/2003 | Eidem | |
| 2003/0029811 A1 | 2/2003 | Russell | |
| 2003/0066758 A1 | 4/2003 | Bess et al. | |
| 2003/0160005 A1 * | 8/2003 | Martin | 210/748 |
| 2003/0196967 A1 | 10/2003 | Robinson et al. | |
| 2004/0206680 A1 | 10/2004 | Johnson | |
| 2004/0251215 A1 | 12/2004 | Bai et al. | |
| 2005/0016933 A1 | 1/2005 | Perlich et al. | |
| 2005/0161342 A1 * | 7/2005 | Carson et al. | 205/688 |
| 2005/0224369 A1 | 10/2005 | Nyman et al. | |
| 2005/0245784 A1 * | 11/2005 | Carson et al. | 205/687 |
| 2006/0021951 A1 | 2/2006 | Leeuwen et al. | |
| 2006/0091046 A1 | 5/2006 | Rosen et al. | |
| 2006/0113257 A1 | 6/2006 | Fernandez et al. | |
| 2006/0243673 A1 | 11/2006 | van Leeuwen et al. | |

FOREIGN PATENT DOCUMENTS

| | | |
|---|---|---|
| EP | 1340719 A | 9/2003 |
| JP | 2005313078 A | 11/2005 |
| KR | 1995-0008377 A1 | 4/1995 |
| KR | 10-2001-0103789 | 11/2001 |
| KR | 10-0365556 | 11/2001 |
| KR | 2001-0104007 A1 | 11/2001 |
| KR | 20-0337319 B2 | 12/2003 |
| KR | 10-2004-0043834 | 5/2004 |
| KR | 20-0349496 B2 | 5/2004 |
| KR | 10-0675375 | 1/2007 |
| WO | 0051942 | 9/2000 |
| WO | 02072478 A | 9/2002 |
| WO | 2004054932 A | 7/2004 |
| WO | 2005061394 A | 7/2005 |
| WO | 2006058261 A | 6/2006 |
| WO | 2007032577 A | 3/2007 |

OTHER PUBLICATIONS

USPTO Office Action dated Jun. 2, 2011 for U.S. Appl. No. 11/757,332.
Written Opinion of the International Searching Authority dated Jan. 28, 2009 for PCT Application No. PCT/US2008/006773.
Written Opinion of the International Searching Authority dated Feb. 6, 2009 for PCT Application No. PCT/US2008/006772.
Wallace et al., "Total organic carbon analysis as a precursor to disinfection byproducts in potable water: Oxidation technique consideration," J. Environ. Monit. 2002, v. 4, pp. 35-42.
Emmanuel et al, "Toxicological effects of disinfections using sodium hypochlorite on aquatic organisms and its contribution to AOX formation in hospital wastewater," Environment International, v. 30 (2004), pp. 891-900.
Office Action dated Oct. 26, 2011 for co-pending U.S. Appl. No. 11/757,332.
Summary of SIPO Office Action for co-pending Chinese National Phase Patent Application No. 200880025359.7.
Summary of SIPO Office Action for co-pending Chinese National Phase Patent Application No. 200580040948.9.
EPO Office Action dated Jul. 13, 2011 for co-pending European National Phase Patent Application No. 08754774.1.
International Search Report and Written Opinion dated Jul. 21, 2006 for PCT/US05/42828.

* cited by examiner

SYSTEM AND PROCESS FOR TREATMENT AND DE-HALOGENATION OF BALLAST WATER

PRIORITY CLAIM

This application is a Continuation-in-Part of U.S. application Ser. No. 11/037,642, filed Jan. 18, 2005

FIELD OF THE INVENTION

The system and process of this invention relate generally to a system and process for the treatment of ballast water to eliminate marine species and pathogenic bacteria from ballast water. More particularly, the system and process of this invention treats ballast water with hypochlorite produced on-site.

BACKGROUND OF THE INVENTION

Ballast water is used to balance the weight distribution in a marine vessel. Ballast water is pumped into tanks where it is stored to properly balance a vessel for a voyage. Often ballast water is taken on at one port and transported to another where it is emptied into the new port. This common practice has an inherent danger. Releasing the ballast water taken aboard from a distant location can be both harmful to the environment and dangerous to human and animals in a new port.

The introduction of non-native marine life into a new ecosystem can have a devastating effect on the native flora and fauna which may not have natural defenses to the new species. Additionally, harmful bacterial pathogens, such as cholera, may be present in the origination pod. These pathogens can multiply in the ballast tanks over time and cause an outbreak of illness in the area where they are released.

The dangers posed by the marine life and pathogens may be controlled by killing those species present in the ballast water. For the past century, chlorination has become the standard way to disinfect water supplies, potable water, wastewater and swimming pools, for example, to eliminate epidemics of waterborne diseases.

SUMMARY OF THE INVENTION

The present invention provides a system and method for treating ballast water in a marine vessel. Ballast water is piped onto a vessel in one port or harbor and discharged upon reaching another port. On-site hypochlorite generation allows the ballast water to be treated on board the vessel before the ballast water is released in a distant port. Treating the ballast water with hypochlorite generated from the ballast water itself or an alternate salt water source eliminates many of the marine organisms and bacteria which may be transported from the first port and propagated within the ballast water tanks. The elimination of these organisms in turn eliminates the introduction of non-native marine species into the water, and prevents outbreaks of water born diseases such as cholera.

Halogens in the form of halogen-containing oxidizing agents, such as HOCl and HOBr, are produced by hypochlorite generation and intended to kill organisms in ballast water onboard a vessel. When the ballast water containing the halogens is released from the vessel the halogen-containing oxidizing agents are potentially dangerous to the marine flora and fauna around the vessel.

In one embodiment of the system of the invention the system comprises a de-halogenation system to remove the halogens from the ballast water. De-halogenating the ballast water comprises neutralizing the oxidizing agents to form the neutral salts of the halogens. The de-halogenation system comprises a means for measuring the halogen content of the ballast water, a reducing agent source in fluid communication with the ballast water, and a means for controlling the amount of reducing agent supplied to the ballast water. The means for controlling the amount of reducing agent is in communication with the means for measuring the halogen content.

In one aspect of the de-halogenation system, the means for measuring the halogen content of the ballast water can comprise one or more oxidation/reduction potential analyzers for determining the oxidation/reduction potential of the ballast water.

In another aspect of the de-halogenation system, the reducing agent source can comprise a reducing agent tank and a pump in fluid communication with the reducing agent tank. The pump is in communication with the means for controlling the amount of reducing agent.

In an additional aspect, the reducing agent source can comprise any combination of suitable reducing agents. Examples of suitable reducing agents include sodium sulfite, sodium metabisulfite, sodium bisulfite, sulfur dioxide, and sodium thiosulfate.

In another embodiment of the de-chlorination system, the system further comprises a means for verifying the effectiveness of the de-halogenation of the ballast water.

In an additional embodiment, the system for treating ballast water of the present invention comprises one or more hypochlorite electrolytic cells and a de-halogenation system. The hypochlorite electrolytic cells are in fluid communication with a salt water source and one or more ballast water tanks. The de-halogenation system is in fluid communication with the ballast water tanks.

In another embodiment, the system for treating ballast water further comprises a means for discharging the ballast water from the ballast water tanks. In one aspect, the means for discharging the ballast water from the ballast water tanks can comprise one or more discharge pumps in fluid communication with the ballast water tanks and discharge piping in fluid communication with the discharge pumps. The discharge piping defines a discharge opening to outside of the vessel. The de-halogenation system can be in fluid communication with the means for discharging the ballast water from the ballast water tanks.

In additional embodiments of the system for treating ballast water, the system can comprise any combination of a means for controlling hypochlorite generation, a flow meter for measuring ballast water flow rate, a total organic carbon analyzer for measuring total organic carbon content of the ballast water, a means for verifying the effectiveness of the ballast water treatment, and a means for verifying the effectiveness of the de-halogenation of the ballast water.

In one embodiment of the process of this invention, the process comprises de-halogenating the ballast water onboard a vessel by measuring the oxidation/reduction potential of the ballast water. One or more reducing agents are added to the ballast water to de-halogenate the ballast water in response to the measured oxidation/reduction potential. In one aspect, the amount of reducing agent added to the ballast water can be modulated to maintain an oxidation/reduction potential measurement that indicates excess reducing agent is present in the ballast water. In another aspect, the oxidation/reduction potential can be maintained at less than about 200 mV. In still another aspect, the oxidation/reduction potential is maintained at about 0 mV.

The oxidation/reduction potential of the ballast water can be measured at any suitable site. Examples of suitable sites include within the one or more ballast water tanks, downstream from the ballast water tanks, upstream from one or more ballast water discharge pumps, downstream from the ballast water discharge pumps, prior to the addition of reducing agent, and after the addition of reducing agent.

In additional embodiments of the de-halogenation process, the process can further comprise any combination of recording the oxidation/reduction potential of the ballast water at timed intervals, providing the recorded oxidation/reduction potentials to a regulatory agency, and removing the recorded oxidation/reduction potentials with a portable data recording device.

In a further embodiment, the process comprises treating the ballast water with generated hypochlorite and de-halogenating the ballast water. The process comprises drawing ballast water onboard a vessel and feeding the ballast water to one or more ballast tanks. Salt water from a salt water source is piped to the one or more hypochlorite electrolytic cells. An amperage is applied to the one or more hypochlorite electrolytic cells to produce hypochlorite within the salt water. The salt water comprising hypochlorite is introduced to the ballast water. The halogen content of the ballast water is measured with a means for measuring halogen content. Reducing agent is added to the ballast water in response to the measured halogen content to de-halogenate the ballast water prior to discharge from the vessel.

In one aspect, the salt water source comprises a side stream removed from the ballast water. In another aspect, the means for measuring halogen content comprises one or more oxidation/reduction potential analyzers.

In another embodiment, the process for treating ballast water further comprises measuring the oxidation/reduction potential of the ballast water and adding a reducing agent to the ballast water to de-halogenate the ballast water in response to the measured oxidation/reduction potential. The ballast water is then discharged from the vessel. In one aspect, the amount of reducing agent added to the ballast water is modulated to maintain an oxidation/reduction potential measurement that indicates excess reducing agent is present in the ballast water. In another aspect, the process further comprises measuring and recording the oxidation reduction potential of the combined ballast water and side stream to confirm that excess halogen is present. Optionally, residual halogen can be maintained at a concentration of at least 1 ppm.

In a further embodiment, the process further comprises measuring and recording process data. Examples of process data which may be recorded include ballast water flow rate, amperage applied to the hypochlorite electrolytic cells, voltage of the hypochlorite electrolytic cells, oxidation/reduction potential of the ballast water and side stream combined, and oxidation/reduction potential of the ballast water prior to discharge from the vessel.

In additional embodiments, the amount of hypochlorite generated may be controlled by modulating the amperage applied to the hypochlorite electrolytic cells. The hypochlorite generated may be controlled in response the measured flow rate of the ballast water or the total organic carbon content of the ballast water. In another aspect, the amount of hypochlorite generated can be controlled to ensure that excess halogen exists in the ballast water.

DETAILED DESCRIPTION

The present invention provides a system and process for treating ballast water. One preferred on-site reaction for creating sodium hypochlorite (NaOCl) is illustrated in the following equation:

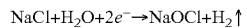

$$NaCl + H_2O + 2e^- \rightarrow NaOCl + H_2 \uparrow$$

Figure 1:
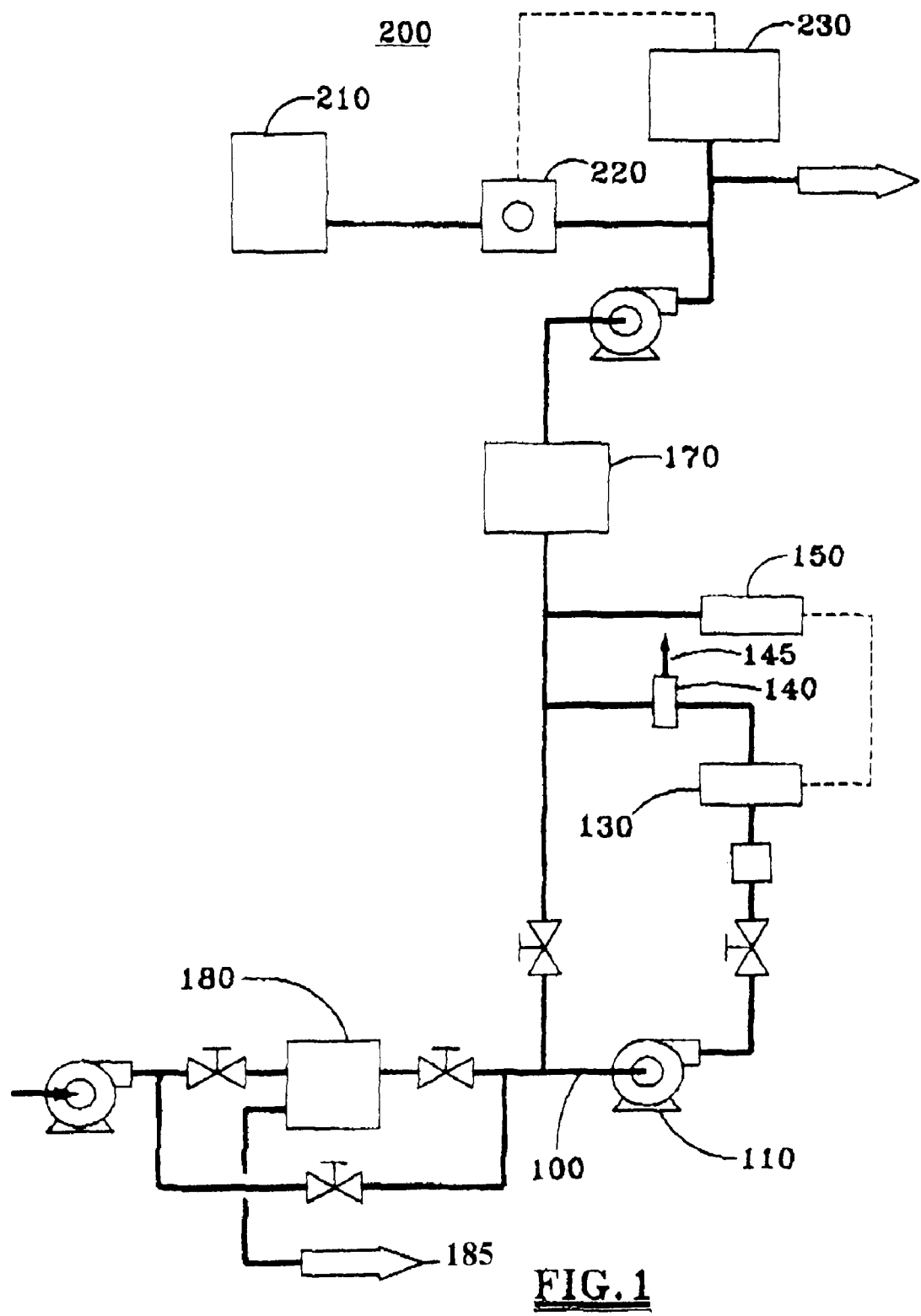
FIG. 1 is a schematic of this invention's system for treating ballast water.
Figure 2:
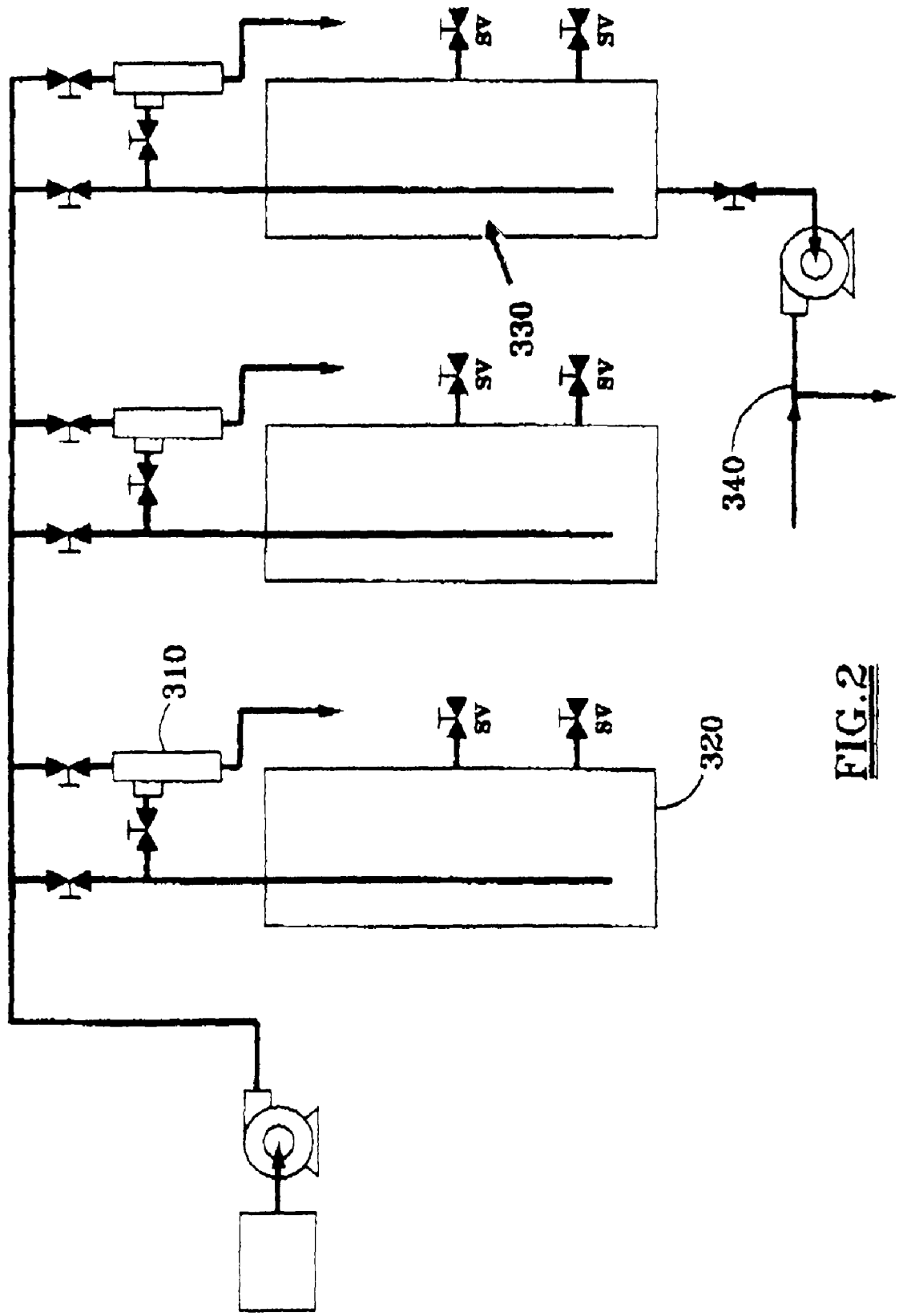
FIG. 2 is a schematic of this invention's system for neutralizing chlorine.

Referring to FIG. 1, in one preferred embodiment of the invention in which the ballast water is treated on-site, water is pumped on board a marine vessel, a ship or oil rig, for example. The water is either seawater with natural salt content or freshwater. In one embodiment, a side stream of ballast water is separated from the main water stream going to the ballast tanks 170. In an alternative embodiment, the side stream is drawn from the ballast water tanks 170 after the main ballast water stream has entered the ballast water tanks 170. The side stream flows through the side stream piping 100 to one or more hypochlorite electrolytic cells 130 where hypochlorite is generated either from the salt naturally present in the ballast water, if seawater, or from added chloride salts if fresh water. Seawater is used for the purposes of this description, but this invention is not limited to seawater. Any chlorine-generating salt water may be used.

The one or more electrolytic cells are equipped with electrodes energized under direct anodic and cathodic current. In this condition partial electrolysis of sodium chloride (NaCl) contained in raw seawater occurs. The aqueous solution of sodium chloride (NaCl), which is completely dissociated as sodium ion (Na+) and chlorine ion (Cl$^-$), reacts at the anode to generate free chlorine. The hydroxide ions (OH$^-$) in the water migrate from the cathodic area and react with Na+ and Cl$_2$ near the anode to produce sodium hypochlorite (NaOCl) and hydrogen (H$_2$).

Sodium hypochlorite in water hydrolyzes to form hypochlorous acid (HOCl). Some of the HOCl reacts with the bromine in the water to form hypobromous acid (HOBr). HOCl and HOBr act as the killing agents used to treat the ballast water.

In one aspect, the water can then flow into a hydrogen separator 140 where the hydrogen byproduct (H$_2$) of the hypochlorite generation is separated from the side stream. The side stream is then reintroduced to the ballast water stream to kill marine organisms and bacteria in the ballast water tanks.

In one embodiment of the invention, the hydrogen separator 140 can comprise a hydrocyclone separator. The hydrogen separator 140 can also comprise a means for venting hydrogen to the atmosphere 145. Additionally, the hydrogen separator 140 can comprise a tube with a pressure relief valve to allow the hydrogen to separate from the liquid. Separating hydrogen from the water stream is important, as hydrogen is highly flammable. Hydrogen is flammable in air in concentrations as low as 4.1% and as high as 74%. Without the use of a hydrogen separator 140, it is possible for hydrogen to be introduced into the ballast water tanks where it could potentially reach hydrogen-air concentrations in the flammability range.

One hydrocyclone separator 140 of this invention comprises a cylindrical top section and a conical bottom section. Water from the one or more electrolytic cells, containing hydrogen, enters the side of the top section. The hydrogen exits the top of the separator, while the water exits the bottom. The water enters tangentially to the side of the cylindrical section so that the water travels in a circular path around the cylindrical and conical sections before flowing out the bottom of the separator, facilitating the separation of the water and hydrogen.

In another embodiment of the invention, a chlorine analyzer 150, in fluid communication with the ballast water stream, measures the chlorine content of the ballast water. The chlorine analyzer 150 can be positioned downstream from the one or more electrolytic cells 130. In one aspect, the chlorine analyzer 150 is positioned downstream from the point where the chlorinated side stream (treatment stream) reenters the ballast water stream. The chlorine analyzer 150 may further comprise a sampling unit that modulates the hypochlorite content in ballast water by measuring the chlorine level in the water and emitting a signal to the electrolytic cells 130 to adjust the amount of hypochlorite generated in the side stream relative to a predetermined concentration in the ballast tank and piping. The chlorine analyzer 150 functions by taking a sample and mixing it with an acidic iodide or potassium iodide reagent. The chlorine present in the sample oxidizes the iodide to iodine. The liberated iodine is measured by a membrane-covered, amperometric type sensor. The level of iodine is proportional to the total chlorine concentration in the sample.

Figure 5:
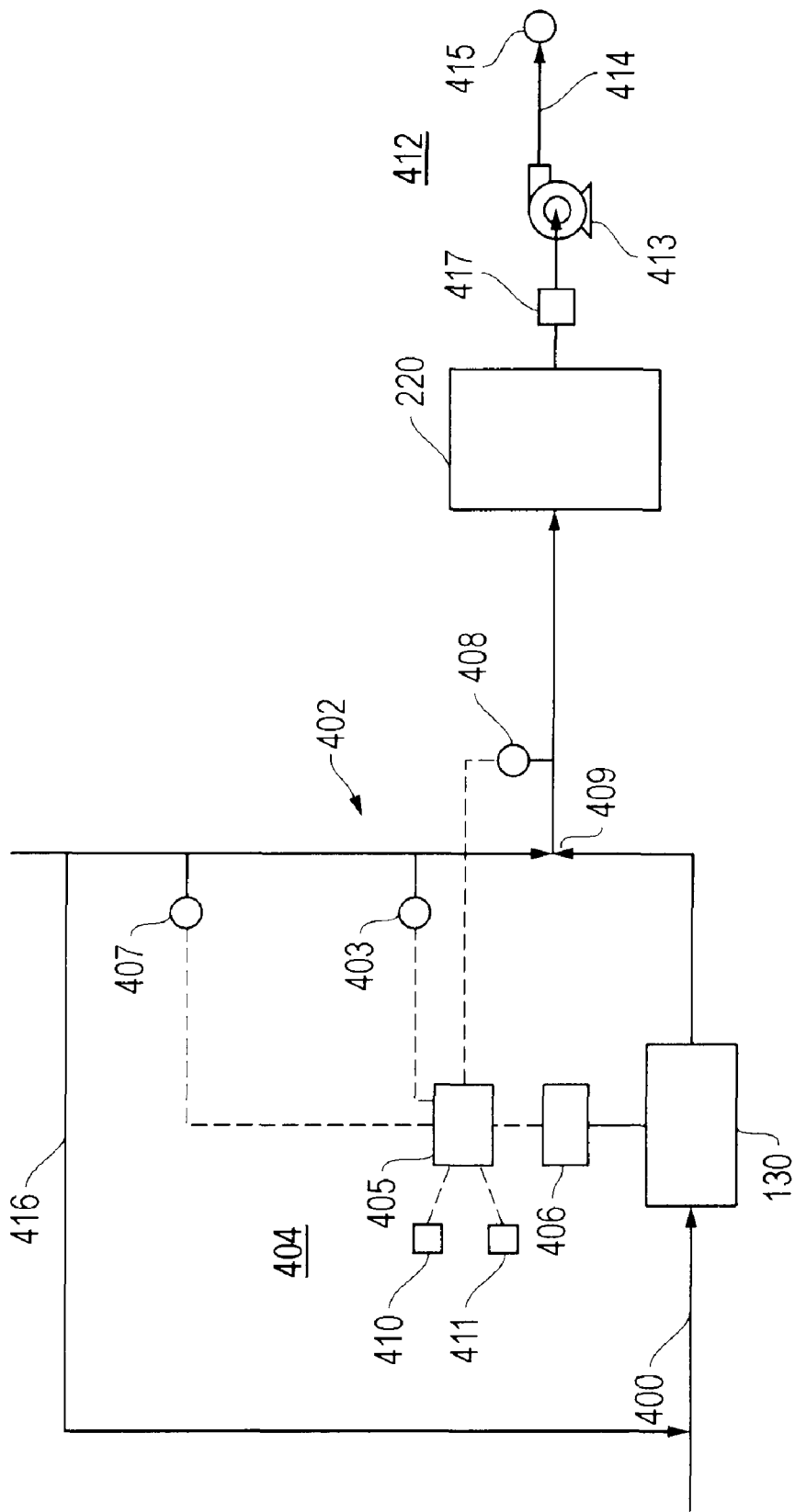
FIG. 5 is a schematic of one embodiment of the system for treating ballast water.

Referring now to FIG. 5, an alternative embodiment of the system comprises a total organic carbon analyzer. In this embodiment, the system for treating ballast water comprises one or more hypochlorite electrolytic cells 130 in fluid communication with a salt water source 400. The salt water source can be a side stream 416 of the ballast water drawn onboard the vessel, water already in the ballast water tanks 220, a sea chest, a separate salt water tank, or any other source. The hypochlorite electrolytic cells 130 are also in fluid communication with the ballast water 402. Hypochlorite produced within the salt water by the hypochlorite electrolytic cells 130 is added to the ballast water. This addition can be made either in the stream of ballast water drawn onboard the vessel, directly to the ballast tanks, or at any other suitable location.

A total organic carbon analyzer 403 is also in fluid communication with the ballast water 402. A total organic carbon (TOC) analyzer 403 is a device which measures the concentration of carbon in water from organic sources, such as microorganisms, plant materials, algae, humic materials, organic acids, and mineral compounds of organic origin. Total organic carbon analyzers are available from the manufacturers O.I. Analytical and HATCH instruments. As a general rule, it is known in the art that about 1 ppm of chlorine is required to neutralize about 1 ppm of TOC.

The system further comprises a means for controlling hypochlorite generation 404 in communication with the total organic carbon analyzer 403. While the means for controlling hypochlorite generation 404 can comprises any suitable equipment, in one embodiment it comprises a control system 405 in communication with the total organic carbon analyzer 403 and a power source 406 that is electrically connected to the hypochlorite electrolytic cells 130. The control system 405 can adjust the amperage applied to the hypochlorite electrolytic cells 130 in response to the TOC measurement.

In another embodiment, the system further comprises a flow meter 407 in fluid communication with the ballast water 402. The flow meter 407 is in communication with the means for controlling hypochlorite generation 404. The flow meter 407 can be placed in the ballast water stream drawn onboard the vessel to measure the ballast water flow rate. The means for controlling hypochlorite generation 404 can utilize the ballast water flow rate and the TOC measurement to determine the amount of hypochlorite required to be generated to kill the organisms in the ballast water and thus the amperage that must be applied to the hypochlorite electrolytic cells 130 to generate the hypochlorite.

In yet another embodiment, the system comprises an oxidation/reduction potential analyzer 408 in addition to the TOC analyzer. In general, an oxidation/reduction potential (ORP) analyzer measures voltage across a circuit formed by a reference electrode and a measurement electrode, with the subject solution between the electrodes. The oxidation/reduction potential of the ballast water is relative to the concentration of the HOCl and HOBr oxidizing agents in the ballast water. Both HOCl and HOBr are oxidizing agent forms of halogens chlorine and bromine. Oxidizing agents steal electrons from the unwanted plants and animals in the ballast water, altering their chemical makeup and killing them. The oxidation/reduction potential analyzer is in fluid communication with the ballast water. The ORP analyzer 408 communicates the oxidation/reduction potential to the means for controlling hypochlorite generation 404. When the OPR analyzer 408 is placed downstream from the point of addition 409 of the hypochlorite to the ballast water, the means for controlling hypochlorite generation 404 can use the measurement to confirm the existence of excess halogen in the form of an oxidizing agent in the ballast water to ensure that enough hypochlorite is present to kill all microorganisms in the ballast water.

In still another embodiment, the system comprises a means for recording system data 410. The means for recording system data 410 can comprise any data recording equipment known in the art. Examples of such data recording equipment include computerized equipment, such as hard drives flash memory, CD-ROM's, and magnetic disks, as well as non-computerized recording equipment, such as paper plots. System data to be recorded can include any data desirable to one skilled in the art, including but not limited to, ballast water flow rate, amperage applied to and cell voltage of the hypochlorite electrolytic cells 130, oxidation/reduction potential of the ballast water 402 and side stream 416 combined, and oxidation/reduction potential of the ballast water prior to discharge from the vessel.

In a further embodiment, the system can comprise a means for verifying the effectiveness 411 of the ballast water treatment. The means for verifying the effectiveness of the ballast water treatment can be included within the means for recording system data 410 or the means for controlling hypochlorite generation 404. The means for verifying the effectiveness of the ballast water treatment can comprise any means known in the art to demonstrate to a regulatory authority, such as the Coast Guard or Port Authority, that ballast water treatment was properly performed, including but not limited to, a plot of system data, a removable hard drive or flash drive, downloading system data on a laptop computer or a handheld device, transferring system data over the internet, or wirelessly transmitting system data to an off vessel location. The regulatory authority may use this information to confirm that the ballast water was properly treated.

In still a further embodiment, the system comprises one or more ballast water tanks 220 and a means for discharging 412 the ballast water from the ballast tanks 220. The means for discharging 412 the ballast water can comprise any suitable combination of pumps, siphons, and piping to remove the ballast water from the ballast tanks and the vessel. In one aspect, the means for discharging 412 the ballast water from the ballast tanks 220 comprises one or more discharge pumps 413 in fluid communication with the ballast tanks 220, discharge piping 414 in fluid communication with the discharge pumps 413, and a discharge opening 415 to outside the vessel.

In an additional embodiment, the system can comprise a means for de-halogenating 417 the ballast water. The means for de-halogenating 417 the ballast water can comprise a sulfite auxiliary system 200 or a de-halogenation system 500. For the purposes of this invention, "de-halogenation" means neutralization of the oxidizing agent form of the halogen.

Referring again to FIG. 1, in another alternative embodiment of this invention, a filter 180 is present and in fluid communication with the ballast water stream. The filter can be positioned upstream from the side stream leading to the one or more electrolytic cells to remove debris from the side stream. The filter is preferably a 50-micron self-cleaning filter. A self-cleaning filter measures the pressure differential across the filter. As the filter screen becomes clogged with the debris removed by the filter, the pressure differential increases. Once the pressure differential reaches a certain setpoint or a predetermined amount of time has lapsed, the filter screen is cleaned by a suction scanner with nozzles that spiral across the inner surface of the screen. The filtration debris is vacuumed from the screen and expelled out the exhaust valve.

In another embodiment of the invention, the hypochlorite electrolytic cell comprises a tubular cell. The tubular cell comprises an outer monopolar tube and inner bipolar tube. The hypochlorite electrolytic cell can also comprise other types of electrolytic cells. Many types of hypochlorite electrolytic cells are known within the onsite, electrochlorination industry. Other types of electrolytic cells include a plate type hypochlorite generator. The electrolytic cell is selected because of its configuration of connection nodes to the electrodes and the hydraulic flow of liquid throughout the cell.

In still another embodiment of the invention, a booster pump 110 is connected to the side stream piping 100 to increase the pressure of water through the ballast water treatment system. Increased pressure is necessary because a substantial pressure drop occurs as the side stream passes through the hypochlorite electrolytic cells 120, which must be compensated for in order to allow the side stream to be reintroduced into the ballast water stream. The booster pump 100 can be positioned either upstream or downstream from the hypochlorite electrolytic cells 120.

Ballast water is typically taken aboard in one port or harbor and then released at the next harbor. Residual halogens, like chlorine and bromine in the form of oxidizing agents HOCl and HOBr, in the ballast water tanks that is not consumed in the treatment of the ballast water is potentially harmful to the marine ecosystem in the new harbor where the ballast water is discharged. The residual chlorine could kill native flora and fauna in the ecosystem. Consuming or neutralizing this residual chlorine immediately prior to discharging the ballast water protects against damage which the residual chlorine would cause. In one embodiment of the invention, a de-chlorination system 200 can be added to neutralize residual chlorine in the ballast water tank 170 before the ballast water is released from the vessel into the port, ocean, lake, or river. The de-chlorination system can be positioned downstream from the ballast tanks. In one embodiment illustrated in FIG. 1, the de-chlorination system can comprise a sulfite auxiliary system. The sulfite auxiliary system 200 can comprise a sulfite tank 210, a pump 220, and a sulfite analyzer 230. In one aspect, the pump of the sulfite auxiliary system 200 is a diaphragm-metering pump. The diaphragm metering pump controls the flow of sulfite used to neutralize residual chlorine.

The sulfite auxiliary system 200 removes residual chlorine by reacting the chlorine with sulfur dioxide gas, a solution of sodium bisulfite, or sodium sulfite. The residual chlorine is consumed in the following reaction,

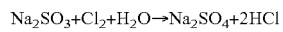

$$Na_2SO_3 + Cl_2 + H_2O \rightarrow Na_2SO_4 + 2HCl$$

So long as excess sulfite ions are present in the effluent, effectively no chlorine is present. The sulfite analyzer converts the sulfite ions in the treated water sample to sulfur dioxide by mixing the sample with acid. The sulfur dioxide is then stripped from the sample and measured by a gas sensor. The analyzer 230 provides a control output to control the feed from the sulfite tank to de-chlorinate the ballast water stream.

Figure 6:
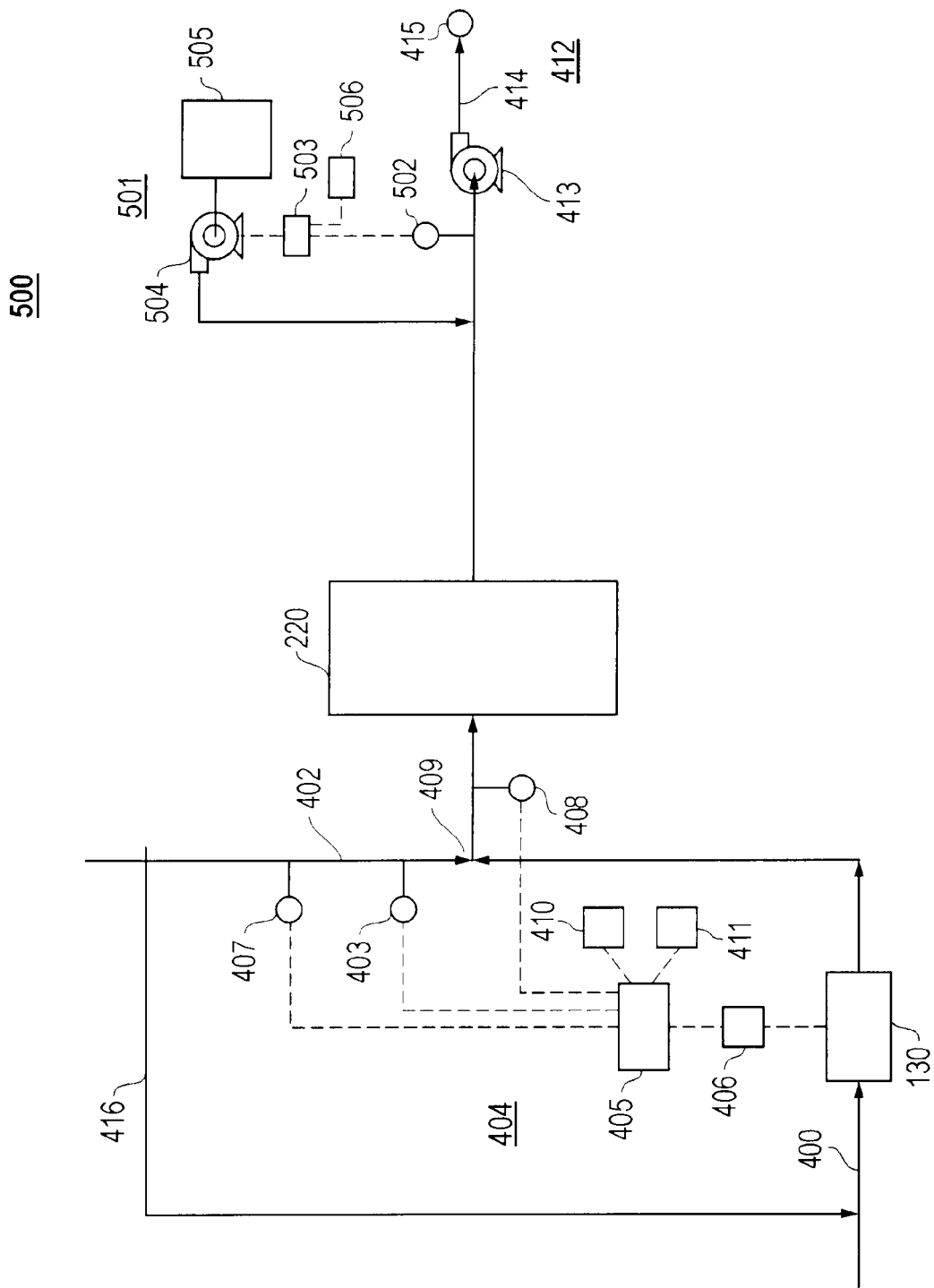
FIG. 6 is a schematic of one embodiment of the system for de-halogenating ballast water.

Alternatively, as shown in FIG. 6 a de-halogenation system 500 can be employed for de-halogenating ballast water. Halogens, including chlorine and bromine in the form of oxidizing agents HOCl and HOBr, are potentially hazardous to marine life if released from the vessel. De-halogenating the ballast water comprises neutralizing oxidizing agent forms of the halogens to create neutral salt derivatives of the halogens which are no longer oxidizing agents. The de-halogenation system comprises a means for measuring the halogen content 502 of the ballast water, a reducing agent source 501 in fluid communication with the ballast water, and a means for controlling the amount of reducing agent 503 supplied to the ballast water. The means for controlling the amount 503 of reducing agent is in communication with the means for measuring the halogen content 502.

The means for measuring halogen content 502 can comprise one or more oxidation/reduction potential analyzers, one or more chlorine analyzers, or wet chemical analysis with potassium iodine indicator and sodium thiosulfate titration. The means for controlling the amount of reducing agent 503 can comprise any combination of equipment known in the art, including, but not limited to, a control system, a computer, a programmable logic controller, and a pump.

In one aspect, the reducing agent source 501 can comprise a reducing agent tank 505 and a pump 504 in fluid communication with the reducing agent tank 505. The pump 504 is in communication with the means for controlling the amount of reducing agent 503. Suitable pumps include a variable dosing pump.

In another aspect, the reducing agent source 501 can comprise one or more suitable reducing agents. Examples of suitable reducing agents include sodium sulfite, sodium metabisulfite, sodium bisulfite, sulfur dioxide, and sodium thiosulfate.

In still another aspect, the de-halogenation system 500 comprises a means for verifying the effectiveness of the de-halogenation 506 of the ballast water. The means for verifying the effectiveness of the de-halogenation 506 of the ballast water can comprise any means known in the art to demonstrate that the ballast water was properly de-halogenated, including, but not limited to, a plot of system data, a removable hard drive or flash drive, downloading system data on a laptop computer or a handheld device, transferring system data over the internet, or wireles sly transmitting system data to an off-vessel location. Optionally, the means for verifying the effectiveness of the de-halogenation 506 can be included in the means for controlling amount of reducing agent 503. A regulatory authority can use this data to confirm that the ballast water was properly de-halogenated.

In another embodiment of the system for treating ballast water, the system comprises one or more hypochlorite electrolytic cells 130 in fluid communication with a salt water source 400 and one or more ballast water tanks 220, and a de-halogenation system 500 in fluid communication with the ballast water tanks 220. In one embodiment, salt water source 400 can be a side stream 416 of the ballast water drawn onboard the vessel.

In one aspect, the system can comprise a means for discharging 412 the ballast water from the ballast tanks. In one embodiment, the means for discharging 412 the ballast water from the ballast tanks 220 comprises one or more discharge pumps 413 in fluid communication with the ballast tanks 220, and discharge piping 414 in fluid communication with the discharge pumps 413. The discharge piping 414 can define a discharge opening 415 to allow the ballast water to be removed from the vessel. In another aspect, the de-halogenation system 500 is in fluid communication with the means for discharging 412 the ballast water from the ballast tanks.

In yet another aspect, the system can further comprise a means for controlling hypochlorite generation 404. Additionally, the system can comprise a flow meter 407 for measuring ballast water flow rate. The flow meter is in communication with the means for controlling hypochlorite generation 404.

In still another aspect, the system can further comprise a means for verifying the effectiveness of the ballast water treatment 410. The system can also comprise a means for verifying the effectiveness of the de-halogenation 506 of the ballast water. Optionally, both the means for verifying the effectiveness of the ballast water treatment 410 and the means for verifying the effectiveness of the de-halogenation 506 of the ballast water can be included within the means for controlling the hypochlorite generation 404.

In one embodiment of a method of this invention, ballast water is treated by first drawing a ballast water stream on board the vessel. The ballast water stream may then be filtered. A portion of the filtered ballast water stream is drawn off through the side stream piping 100 to form a treatment stream. This treatment stream is piped to hypochlorite electrolytic cells, where a current is applied to the cells to produce hypochlorite within the treatment stream. Hydrogen, which is flammable, is separated from the treatment stream before the treatment stream is reintroduced into the main ballast water stream. The ballast water stream containing the hypochlorite is sampled after the treatment stream is reintroduced to the ballast water stream to determine the chlorine concentration of the ballast water stream.

In one aspect of the method of this invention, the treatment stream is removed from the ballast water stream before the stream enters the ballast water tank. Alternatively, the treatment stream is drawn off of the ballast water tanks. The treatment stream is then treated with hypochlorite and reintroduced into the ballast water stream before the stream enters the ballast water tank. The hypochlorite electrolytic cells use natural salt water when the ballast water tanks take on seawater, to generate hypochlorite in the treatment stream. Alternatively, if fresh water is used as ballast water, a sodium chloride salt can be added to the fresh water to supply the chloride ion.

In an alternative embodiment of the method, the pressure of the treatment stream, which drops as the stream enters the side stream piping 100, is increased with a pump. In another preferred embodiment of the method, the ballast water stream is filtered prior to entering the treatment stream. In another embodiment of the method, hydrogen is separated from the treatment stream by a hydrocyclone separator.

In another embodiment of the method, the ballast water stream is sampled after the treatment stream is reintroduced into the ballast water to determine the chlorine concentration of the ballast water stream. The chlorine concentration of the ballast water stream is measured by a chlorine analyzer. The current in the hypochlorite electrolytic cells is adjusted in response to the measured chlorine concentration to increase or decrease the hypochlorite generated in the treatment stream to achieve the proper concentration of hypochlorite in the ballast water tank.

In one embodiment of the process of this invention, the process for treating ballast water comprises ascertaining the total organic carbon content of the ballast water. The total organic carbon content can be ascertained in any suitable manner including measuring with a total organic carbon analyzer, obtaining a value from a reference source, and sampling the ballast water and measuring TOC content with analytical equipment. When measuring the total organic carbon content of the ballast water, a measurement or sample can be taken at any suitable location, including in the incoming ballast water, the water outside the vessel, and the water in the ballast tanks.

To generate hypochlorite, salt water from a salt water source 400 is piped to one or more hypochlorite electrolytic cells 100. In one aspect of the process, the salt water source can be a side stream 416 of the ballast water drawn onboard the vessel. An amperage is applied to the one or more hypochlorite electrolytic cells to produce the hypochlorite within the salt water. The salt water comprising hypochlorite is introduced to the ballast water to treat the ballast water. In one embodiment, the hypochlorite is introduced to the ballast water upstream of the ballast water tanks to facilitate mixing of the hypochlorite and ballast water. Hypochlorite production by the hypochlorite electrolytic cells is modulated in response to the total organic carbon content of the ballast water. The higher the TOC content of the ballast water the greater the amount of hypochlorite that must be produced.

In another embodiment of the process, the step of modulating hypochlorite production by the hypochlorite electrolytic cells in response to the total organic carbon content comprises adjusting the amperage applied to the hypochlorite electrolytic cells. Increasing amperage results in increased hypochlorite production. In one aspect, hypochlorite production is modulated to maintain residual halogen in the ballast water. Residual halogen is halogen-containing oxidizing agent in excess of the amount required to kill all the microorganisms present in the ballast water. The presence of residual halogen in the ballast water ensures that no microorganisms remain in the ballast water that can multiply in the ballast water tanks. In another aspect, hypochlorite production by the hypochlorite electrolytic cells in modulated so that the weight ratio of hypochlorite in the ballast water to total organic carbon in the ballast water ranges from about 1.0 to about 3.0. A weight ratio greater than 1.0 should maintain residual halogen in the ballast water.

In an additional embodiment of the process, ballast water is drawn onboard the vessel and the flow rate of the ballast water is measured. The flow rate is combined with the TOC content of the ballast water to determine a hypochlorite generation rate required to treat the ballast water.

In one aspect of the process, process data can be measured and recorded. Examples of process data include total organic carbon content of the ballast water, ballast water flow rate, amperage applied to the hypochlorite electrolytic cells, oxidation/reduction potential of the ballast water and salt water comprising hypochlorite combined, and oxidation/reduction potential of the ballast water prior to discharge from the vessel.

In still another aspect of the process, residual halogen in the ballast water produced by the electrolytic cells in response to the TOC content can be removed by de-halogenating the ballast prior to discharge from the vessel.

In an alternative method of this invention, ballast water is treated by drawing a ballast water stream onto a marine vessel, filtering the ballast water stream, and removing a portion of the filtered ballast water stream to form a treatment stream. The pressure of the treatment stream is increased. The treatment stream is then piped to hypochlorite electrolytic cells, where a current is applied to the cells to produce hypochlorite within the treatment stream. Hydrogen is separated from the treatment stream by a means for venting. The treatment stream is reintroduced into the ballast water stream. The ballast water stream is sampled after the treatment stream is reintroduced to determine the chlorine concentration of the ballast water stream. The current in the one or more hypochlorite electrolytic cells is adjusted in response to the measured concentration to increase or decrease the hypochlorite generated in the treatment stream. The treated ballast water stream can then piped to the ballast tanks. Finally, prior to discharge, residual chlorine is neutralized in the ballast water stream downstream from the one or more hypochlorite electrolytic cells with sulfite.

In one embodiment of the method, hydrogen is separated from the treatment stream by a hydrocyclone separator. Alternatively, the means for venting hydrogen can comprise venting the ballast water tanks to the atmosphere.

In another embodiment of the method, the step of neutralizing residual chlorine comprises piping the ballast water stream to a sulfite auxiliary system. The sulfite auxiliary system is positioned downstream from the ballast water tanks.

Residual halogens in the ballast water, such as chlorine and bromine, are potentially hazardous to marine life. In an alternative to de-chlorination as described, the ballast water can be de-halogenated prior to its release from the vessel to eliminate the danger caused by the residual halogen. The process for de-halogenating the ballast water comprises measuring the halogen content of the ballast water with a means for measuring halogen content 503. Reducing agents are added to the ballast water in response to the measured halogen content to de-halogenate the ballast water prior to discharge from the vessel. In one aspect, the reducing agent may be added downstream from the ballast water tank. Examples of suitable reducing agents include sodium sulfite, sodium metabisulfite, sodium bisulfite, sulfur dioxide, sodium thiosulfate, and combinations thereof.

In one embodiment, the process for de-halogenating ballast water onboard a vessel comprises measuring the oxidation/reduction potential of the ballast water. One or more reducing agents are added to the ballast water to de-halogenate the ballast water in response to the measured oxidation/reduction potential. In one aspect, the amount of reducing agent added to the ballast water can be modulated to maintain an oxidation/reduction potential measurement that indicates excess reducing agent is present in the ballast water. When excess reducing agent is present, potentially harmful halogens like chlorine and bromine should not be present. In another aspect, the oxidation/reduction potential is maintained at less than about 200 mV. An OPR of less than 200 mV indicates that excess reducing agent exists. In still another aspect, the oxidation/reduction potential is maintained at about 0 mV.

Examples of suitable sites for measuring oxidation/reduction potential include within the one or more ballast water tanks 220, downstream from the ballast water tanks 220, upstream from one or more ballast water discharge pumps 413, downstream from the ballast water discharge pumps 413, prior to the addition of reducing agent, after the addition of reducing agent, and combinations thereof. In another embodiment of the process, the oxidation/reduction potential of the ballast water can be recorded at timed intervals. The recorded oxidation/reduction potentials can be monitored to confirm that de-halogenation was preformed properly. Optionally, the recorded oxidation/reduction potentials may be provided to a regulatory agency. In another aspect, the recorded oxidation/reduction potentials can be removed from the vessel with a portable data recording device.

The process for treating ballast water can comprise de-halogenating the ballast water. In one embodiment, the process for treating ballast water comprises drawing ballast water 402 onboard a vessel. The ballast water is fed to one or more ballast tanks 220 on the vessel. Salt water is piped from a salt water source 400 to one or more hypochlorite electrolytic cells 130 to generate hypochlorite. The salt water source can be a side stream 416 removed from the ballast water or any other suitable source. An amperage is applied to the one or more hypochlorite electrolytic cells 130 to produce hypochlorite within the salt water. The salt water comprising hypochlorite is introduced to the ballast water to treat microorganisms in the ballast water. In one embodiment, the salt water comprising hypochlorite is added upstream of the ballast tanks to facilitate mixing of the hypochlorite and the ballast water within a pipe.

The halogen content of the ballast water is measured with a means for measuring halogen content 502. One or more reducing agents are added to the ballast water in response to the measured halogen content to de-halogenate the ballast water prior to discharge from the vessel.

In one aspect of the process for treating and de-halogenating ballast water, the means for measuring the halogen content 502 of the ballast water comprises an oxidation/reduction potential analyzer. Optionally, the amount of reducing agent added to the ballast water is modulated to maintain an oxidation/reduction potential measurement that indicates excess reducing agent is present in the ballast water.

In another embodiment of the process for treating and de-halogenating ballast water, the process further comprises measuring and recording the oxidation reduction potential of the combined ballast water and hypochlorite to confirm that excess halogen is present. Excess halogen in the ballast water will ensure that no microorganism will multiply in the ballast water tanks. The halogen will be removed from the ballast water by de-halogenation before discharge from the vessel. In one aspect, the process can further comprise controlling the amount of hypochlorite generated to ensure that excess halogen exists in the ballast water.

In still another embodiment, the process comprises measuring and recording process data. The process data can be later reviewed to determine the effectiveness of the ballast water treatment or de-halogenation. Examples of process data which may be recorded include ballast water flow rate, amperage applied to the hypochlorite electrolytic cells, cell voltage, oxidation/reduction potential of the ballast water and side stream combined, and oxidation/reduction potential of the ballast water prior to discharge from the vessel.

In yet another embodiment of the process, the amount of hypochlorite generated may be controlled by measuring the flow rate of the ballast water and modulating the amperage applied to the hypochlorite electrolytic cells. This method of control is also known as flow pacing. To keep pace with the amount of ballast water drawn onboard the vessel and its inherent microorganism content, the amperage applied to the electrolytic cells is function of the flow rate of the ballast water.

Alternatively, the amount of hypochlorite generated may be controlled in response to the total organic carbon content of the ballast water. Hypochlorite generated can be generated to maintain a weight ratio of hypochlorite to total organic carbon content.

TEST EXAMPLES

Example 1

Sodium Hypochlorite Mesocosm September 2004

The first test of the sodium hypochlorite generator/filtration treatment system was started on Sep. 3, 2004. The experiment included a chlorine/no filtration treatment and chlorine with filtration treatment. The target chlorination level was 4 mg/L. Initial chlorine levels for the filtered treatment were 3.5 mg/L and 2.95 mg/L without filtration. There were 4 mesocosms (tanks) per treatment and 4 control mesocosms. The mesocosms were analyzed for Total Residual Oxidant ($Cl_2$ mg/L), culturable heterotrophic bacteria, chlorophyll a, and zooplankton at 5, 24, 48, 120, and 240 hours following treatment.

Procedure

Total Residual Oxidant

Total Residual Oxidant (TRO) was measured as $Cl_2$ using a Hach Spectrophotometer and Hach Colorimeter. DPD powder pillows were used for the analysis. TRO measurements were after the initial fill and at all of the time points listed above. The 1500-gallon tank of raw seawater was tested for bacteria levels before the start of the experiment. Water samples taken at the 5 time points were also tested for bacteria levels.

Culturable Bacteria

Bacteria colonies were cultured from known volumes of water to calculate colony-forming units (CFU) per liter of water. Colonies were cultured on petri dishes containing a growth medium suited for marine heterotrophic bacteria. The inoculated medium was analyzed for colony formation after a few days at room temperature incubation.

Chlorophyll a

Water samples were also taken for chlorophyll a analysis. Chlorophyll a is an indicator for the presence of live phytoplankton. A known volume of sample water was filtered through glass fiber filters with a pore size small enough to retain phytoplankton cells. The filters were frozen for later analysis in our Seattle laboratory. Chlorophyll a was extracted from the filters using acetone and then analyzed for fluorescence to determine the concentration in μg/L.

Mesozooplankton

Mesozooplankton were collected in Mystery Bay, using a 110 μm mesh net 1 meter diameter the morning of the test. Enough were collected to achieve approximately 150 mesozooplankton per liter. A Stempel pipette was used three times to collect a randomized 5 ml sample of the mesozooplankton "soup". The densities, counted using a dissecting scope, were used to calculate how much of the "soup" was needed for the 1500-gallon tanks to achieve 150 mesozooplankton per liter. The calculated amount of soup was poured into the tank and allowed to settle for at least an hour to let zooplankton acclimate. Three preliminary samples were collected out of the 1500-gallon tank after mixing. These were used to check calculation and to see the effects of the pumps. Sampling periods for mesozooplankton were 5, 24, 48, 120, and 240 hours. Samples were collected out of the 72-gallon mesocosms using a 1-liter Nalgene bottle after thoroughly mixing the contents of the mesocosm. Liter sample was filtered through a 73 μm sieve and placed in counting tray. Mesozooplankton counted were placed into one of eight generic categories and then by state; live, dead (absolutely no response to poking) or moribund (internal movement and no flight response to needle poke).

Results for Example 1

Figure 3:
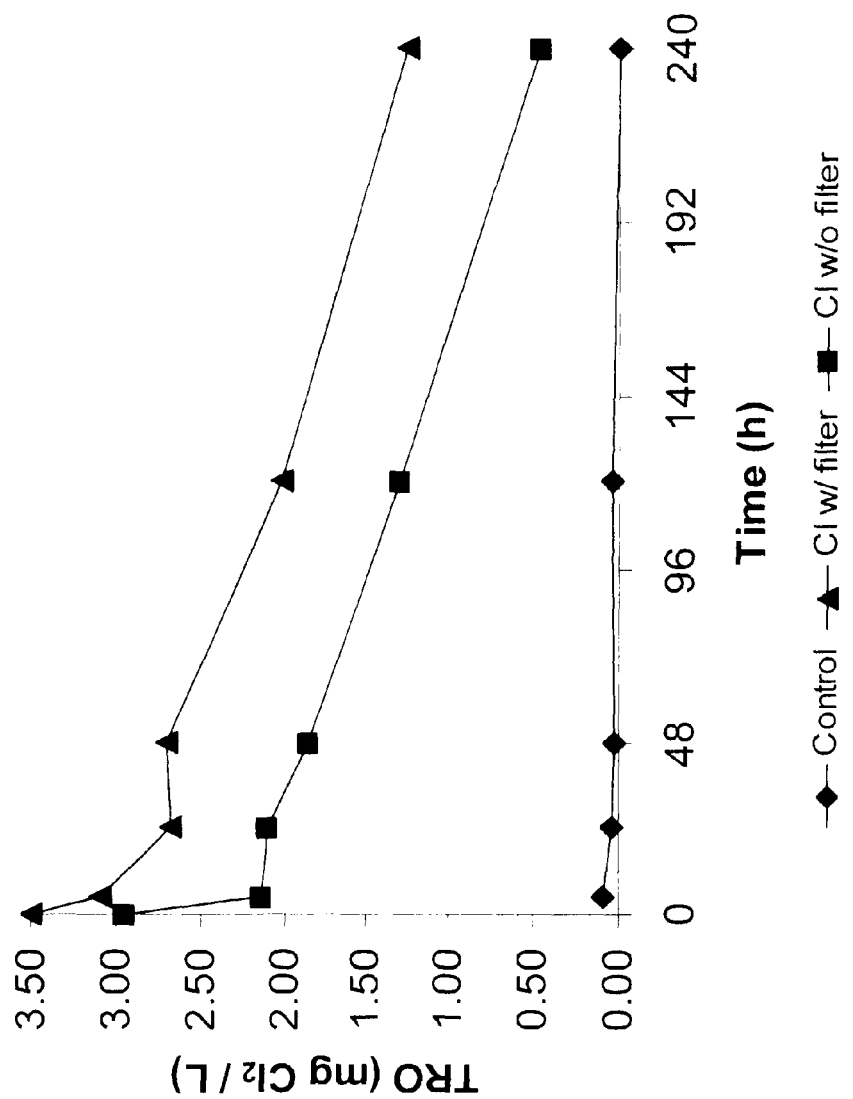
FIG. 3 is a chart showing the experimental results of treating ballast water with the system and method of this invention.

Total Residual Oxidant (TRO) levels declined steadily for the duration of the experiment. (FIG. 3). TRO in the nonfiltered test tanks dropped more than the filtered test tanks in the first 5 hours and then the TRO dissipated equally for the remaining time points.

Bacteria were greatly reduced in both treatments and showed minimal rebound over the 10 days of the experiment. There was a slight rebound of bacteria in the treatment without filtration.

Chlorophyll a is an indicator of phytoplankton. In the treated seawater, Chlorophyll a levels were at or below the detection limit starting with the 5-hour time point and continued to drop for both of the treatments.

In the control tanks, chlorophyll a levels declined over the duration of the experiment, likely due to the absence of light since all of the mesocosms were covered.

After the first treatment trial it was concluded that no statistical difference could be found between the two treatments, at all time points and states. The difference between the control and treatments was highly significant. Some mesozooplankton were still able to get through the 50 μm filter, all were dead except for 2 organisms.

Example 2

Sodium Hypochlorite Mesocosm October 2004

The second test of the sodium hypochlorite generator/filtration treatment system was started on Oct. 12, 2004. Two experiments were performed. The first experiment compared two treatments, filtration/chlorination (~1.0 mg $Cl_2$/L) versus filtration only. The second experiment compared a chlorination dose of 1.0 mg $Cl_2$/L with a dose of 1.6 mg $Cl_2$/L. Each experiment included 4 mesocosms per treatment and 4 control tanks. The mesocosms were analyzed for Total Residual Oxidant (TRO) (mg $Cl_2$/L), culturable heterotrophic bacteria, chlorophyll a, and zooplankton at 5, 24, 48, and 240 hours following treatment. Culturable phytoplankton was enumerated in the first experiment. Samples were also collected at 5 hours for nutrient and total organic carbon (TOC) analysis. The temperature in the mesocosms fluctuated between 12.0° C. and 14.0° C.

Procedure

The procedure for Example 2 was the similar to the procedure used in Example 1 except for the phytoplankton technique.

Phytoplankton Most Probable Number Technique

During the first October experiment we tested the use of the Most Probable Number (MPN) technique, a dilution based culture method, to enumerate viable phytoplankton cells after treatment. Phytoplankton samples were collected from each treatment (control, filtered, and filtered and chlorinated) at four time points (5, 24, 48, and 240 hours). Each sample was filtered onto a glass fiber filter, and this filter (containing phytoplankton cells) was used to inoculate phytoplankton growth medium (f/2) over a dilution series. The inoculations were then transferred to incubators set to optimize growth (12:12 light:dark cycle, 13° C.). The pattern of growth over the dilution series allows for a calculation of the MPN, an estimate of the number of viable phytoplankton cells per L. Using this technique we can determine the effectiveness of a particular treatment at reducing the number of viable phytoplankton by comparing control and treatmentabundance estimates.

Results

Figure 4:
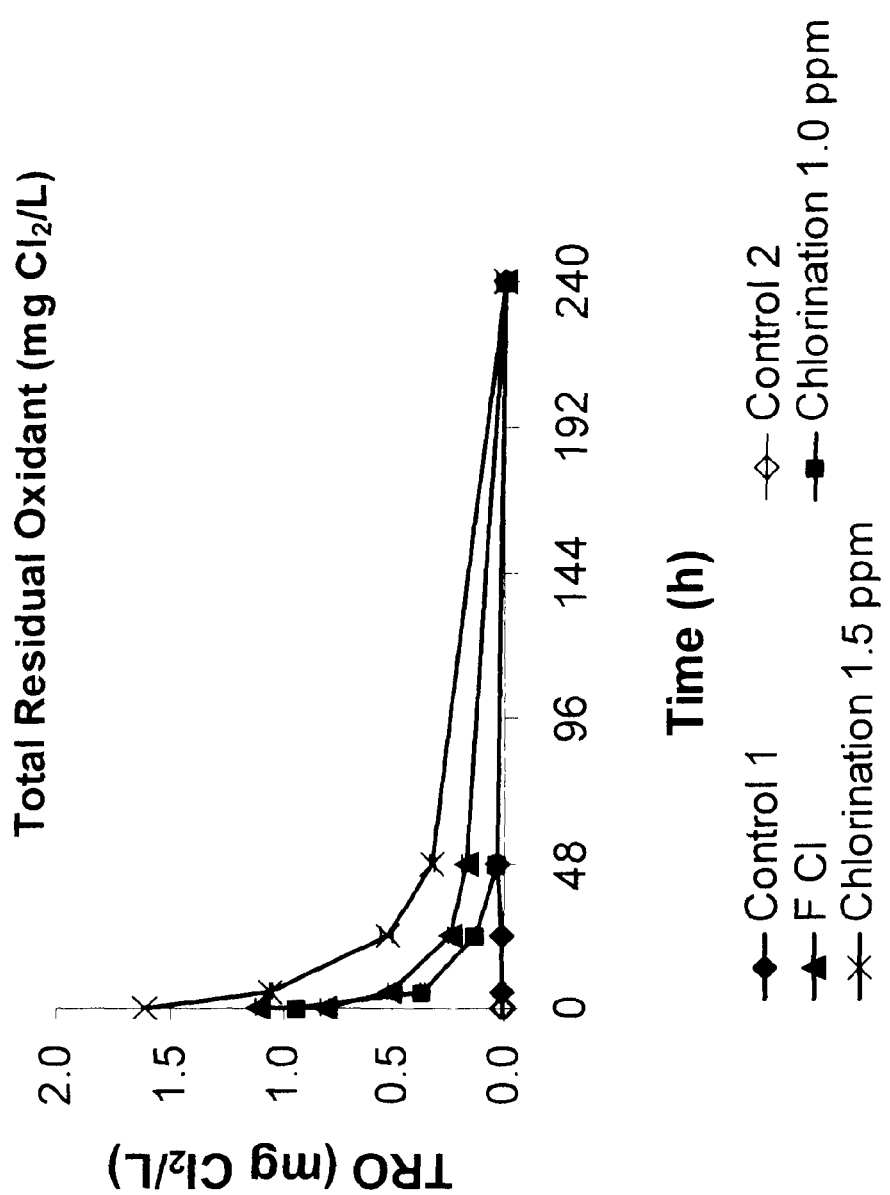
FIG. 4 is another chart showing the experimental results of treating ballast water with the system and method of this invention.

Total Residual Oxidant—The goal of the filtration with chlorination treatment was to dose to an initial TRO level between 0.5 and 1.0 mg $Cl_2$/L. The actual dose achieved had an average TRO of 1.11 mg $Cl_2$/L at the initial filling of the mesocosms (FIG. 4). This TRO declined 54% in the first 5 hours to a TRO of 0.51 mg $Cl_2$/L. TRO degradation slowed with time and completely disappeared by 240 hours. TRO for the chlorination only treatments of the second experiment showed a similar degradation curve. The goal of the chlorination only treatments was to dose with an initial TRO of 1.0 and 1.5 mg $Cl_2$/L. The actual dose averages were 0.94 mg $Cl_2$/L and 1.61 mg $Cl_2$/L TRO. Highest percent reduction of TRO occurred with the lowest TRO dose.

Culturable Bacteria were initially reduced in all 3 of the chlorinated treatments at 5 hours. Although slightly suppressed, bacteria in the chlorinated treatments rebounded to levels higher than the controls by 240 hours. The filtration only treatment showed negligible reduction in bacteria at 5 hours with levels equal to the control treatment at subsequent treatments.

Mesozooplankton—Chlorine plus filtration had an immediate effect upon the zooplankton, reaching a 95% mortality at 5 hours and complete mortality at 24 hours. By 48 hours the high chlorine treatment results were similar to the filtration with chlorination treatment. At 5 hours the filtration with chlorine treatment had no live organisms per L, there were only 1-2 moribund organisms per L at this time. The percent dead of the two controls were similar except for the 48 hours sample.

Chlorophyll a is an indicator of phytoplankton biomass. The filtration with chlorination treatment showed the greatest initial reduction in chlorophyll a compared with the chlorination only treatments. At 5 hours chlorophyll a levels were reduced by 98% for the filtration with chlorination treatment when compared to the control treatment. The filtration only treatment showed slight reduction when compared with the control treatment. In the control tanks, chlorophyll a declined over the duration of the experiment, likely due to the absence of light since all of the mesocosms were covered.

The phytoplankton culture (MPN) technique shows that the number of viable phytoplankton cells was greatly reduced by filtration compared to the control. Some of the inoculations showed positive growth over the entire series of dilutions, thus allowing us to only estimate the MPN as greater than or equal to result. It appears that filtration removes as much as 50% of the viable phytoplankton from the mesocosms. The reduction of viable phytoplankton was more dramatic when water was treated with the combined filtration and chlorination system. Numbers of viable phytoplankton were reduced 99% by this treatment compared to the control.

Although the present invention and its advantages have been described in detail, it should be understood that various changes, substitutions and alterations can be made herein without departing from the spirit and scope of the invention as defined by the appended claims.

The invention claimed is:

1. A process for treating ballast water comprising:
   drawing ballast water onboard a vessel;
   feeding the ballast water to one or more ballast tanks;
   piping salt water from a salt water source to one or more hypochlorite electrolytic cells;
   applying an amperage to the one or more hypochlorite electrolytic cells to generate hypochlorite within the salt water;
   controlling a rate of hypochlorite generation by adjusting the amperage applied to the one or more hypochlorite electrolytic cells based on at least one of:
      a flow rate of the ballast water measured by a flow meter, and
      a total organic carbon content of the ballast water measured by a total organic carbon analyzer;
   introducing the salt water comprising hypochlorite to the ballast water;
   measuring the halogen content of the ballast water with a means for measuring halogen content;
   adding reducing agent to the ballast water in response to the measured halogen content to de-halogenate the ballast water prior to discharge from the vessel.

2. The process of claim 1 wherein the salt water source comprises a side stream removed from the ballast water.

3. The process of claim 1 wherein the reducing agent is selected from a group consisting of: sodium sulfite, sodium metabisulfite, sodium bisulfite, sulfur dioxide, and sodium thio sulfate.

4. The process of claim 1 wherein the step of introducing the salt water comprising hypochlorite to the ballast water comprises:
   introducing the salt water comprising hypochlorite upstream of the of the ballast water tanks.

5. A process for treating ballast water comprising:
   drawing ballast water onboard a vessel;
   removing a portion of the ballast water to form a side stream;
   piping the side stream to one or more hypochlorite electrolytic cells;
   applying an amperage to the one or more hypochlorite electrolytic cells to generate hypochlorite within the side stream;
   controlling a rate of hypochlorite generation by adjusting the amperage applied to the one or more hypochlorite electrolytic cells based on at least one of:
      a flow rate of the ballast water measured by a flow meter, and
      a total organic carbon content of the ballast water measured by a total organic carbon analyzer;
   reintroducing the side stream to the ballast water;
   feeding the ballast water to one or more ballast tanks;
   measuring the oxidation/reduction potential of the ballast water;
   adding a reducing agent to the ballast water to de-halogenate the ballast water in response to the measured oxidation/reduction potential; and
   discharging the ballast water from the vessel.

6. The process of claim 5 wherein the reducing agent is selected from a group consisting of: sodium sulfite, sodium metabisulfite, sodium bisulfite, sulfur dioxide, and sodium thiosulfate.

7. The process of claim 5 wherein the amount of reducing agent added to the ballast water is modulated to maintain an oxidation/reduction potential measurement that indicates excess reducing agent is present in the ballast water.

8. The process of claim 7 wherein the oxidation/reduction potential is maintained at less than about 200 mV.

9. The process of claim 8 wherein the oxidation/reduction potential is maintained at about 0 mV.

10. The process of claim 5 further comprising measuring and recording the oxidation reduction potential of the combined ballast water and side stream to confirm that excess halogen is present.

11. The process of claim 5 further comprising measuring and recording process data.

12. The process of claim 11 wherein the process data comprises one or more parameters selected from a group consisting of: ballast water flow rate, amperage applied to the hypochlorite electrolytic cells, voltage in the hypochlorite electrolytic cells, oxidation/reduction potential of the ballast water and side stream combined, and oxidation/reduction potential of the ballast water prior to discharge from the vessel.

13. The process of claim 5 comprising controlling the amount of hypochlorite generated to ensure that excess halogen exists in the ballast water.

14. The process of claim 5 further comprising measuring the oxidation/reduction potential of the ballast water at one or more sites selected from a group consisting of: within the one or more ballast water tanks, downstream from the ballast water tank, upstream from one or more ballast water discharge pumps, downstream from the ballast water discharge pumps, prior to the addition of reducing agent, and after the addition of reducing agent.

15. The process of claim 14 further comprising recording the oxidation/reduction potential of the ballast water at timed intervals.

16. The process of claim 15 further comprising providing the recorded oxidation/reduction potentials to a regulatory agency.

17. The process of claim 5, further comprising:
    removing a portion of seawater from a secondary seawater source to form a secondary side stream; and
    piping the secondary side stream to the one or more hypochlorite electrolytic cells.

* * * * *